United States Patent [19]

David et al.

[11] Patent Number: 4,559,230

[45] Date of Patent: Dec. 17, 1985

[54] PROTEIN PRODUCT, PROCESS FOR MAKING IT AND PHARMACEUTICAL COMPOSITION CONTAINING SAID PROTEIN

[75] Inventors: Bernard David, Villiers sur Marne; Gabriel Peltre; Salah Mecheri, both of Paris, all of France

[73] Assignee: Institut Pasteur, Paris, France

[21] Appl. No.: 478,108

[22] Filed: Mar. 23, 1983

[30] Foreign Application Priority Data

Mar. 26, 1982 [FR] France .................................. 82 05241

[51] Int. Cl.[4] ..................... A61K 39/36; A61K 39/00; A61K 45/02; A61K 37/00
[52] U.S. Cl. ........................................ 424/91; 424/85; 424/88; 260/112 R; 260/112 B; 514/6; 514/8
[58] Field of Search ................... 424/91, 177, 180, 88, 424/85; 260/112 R, 112 B

[56] References Cited

PUBLICATIONS

Chemical Abstracts, vol. 88, 1978, No. 87459v, p. 354, Topping, M. D. et al., "Fractionation of Cocksfoot . . . by Preparative Isoelectric Focusing".
Chemical Abstracts, vol. 89, 1979, No. 105669r, p. Lowenstein, H., "Immunological Partial Identity . . . Four Grasses".
Chemical Abstracts, vol. 95, 1981, No. 166836p, p. 536, Williams, S. E. et al., "Comparison of Allergenic Extracts . . . Focusing".
Chemical Abstracts, vol. 95, 1981, No. 76296h, p. 378, Hari, V., "A Method for the Two-Dimensional Electrophoresis of Leaf Proteins".
"McGraw-Hill Dictionary of the Life Sciences," pp. 354 and 676.
Journal of Chromatography, 150, (1978), 17–44, "Chromatofocusing: Isoelectric Focusing on Ion-Exchange Columns", Sluyterman et al., pp. 17–44.
Biochimica et Biophysica Acta, 295, (1973), "Isoelectric Focusing in Layers of Granulated Gels", Bertold J. Radola, pp. 412–428.

Primary Examiner—Thomas G. Wiseman
Assistant Examiner—Robin Lyn Teskin
Attorney, Agent, or Firm—Oblon, Fisher, Spivak, McClelland & Maier

[57] ABSTRACT

New product consisting of glycoprotein having a molecular weight of about 14,000 and an isoelectric point of about 4.6, its absorption spectrum having an absorption of $\epsilon = 0.12$ units of optical density (O.D.) at 280 nm for an aqueous solution of 1 mg (dry weight) per ml of water. This product has immunoregulating properties and is useful in allergic therapeutic composition.

20 Claims, 1 Drawing Figure

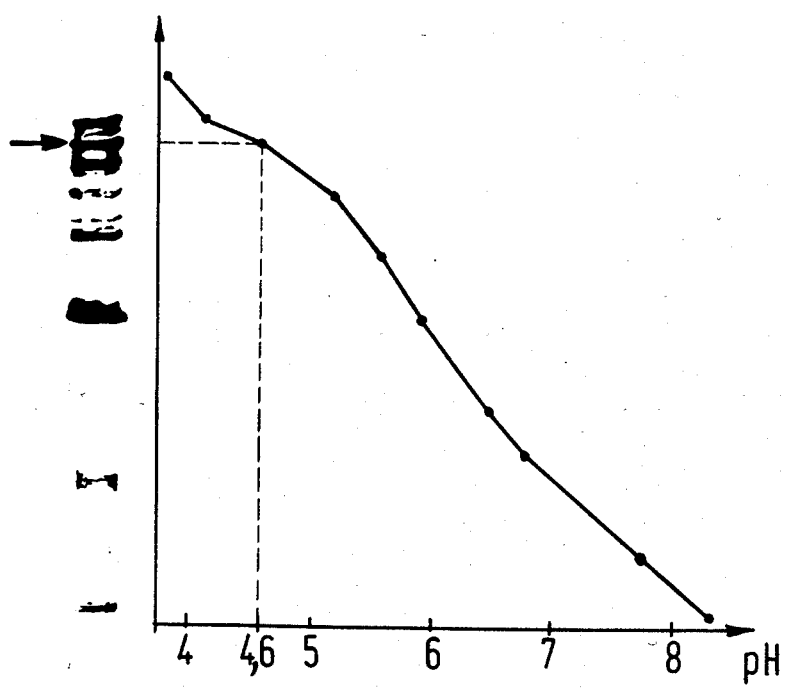

PROTEIN PRODUCT, PROCESS FOR MAKING IT AND PHARMACEUTICAL COMPOSITION CONTAINING SAID PROTEIN

BACKGROUND OF THE INVENTION

1. Field of the Invention

The present invention relates to a new product consisting of a protein. It also relates to a process for isolating such a protein. Another object of the invention is the use of this new product in a therapeutic composition and in particular an immunoregulating and anti-allergic therapeutic composition. In one of its aspects, the invention therefore pertains to the immunological and allergic field.

2. Description of the Prior Art

It is known that allergic manifestations are very frequent and are due to a large number of factors. Allergic illnesses are tenacious owing to the very reason of the constant or occasional presence of factors producing the allergic reactions. It is therefore desirable to increase the immunizing reactions of the organism to improve its resistance to exterior attacks and in particular the factors responsible for the allergic reactions.

Among the causes of allergy plant pollens are often mentioned. One skilled in the art may in this respect refer to the very documentated article of Raymonde BARREAU and Jean-René MALLET in the "Journal de Médecine de Bordeaux" 1958, 135, 1379-1389. This bibliographical reference refers first of all to the social importance of allergic diseases and in particular those due to pollen. Many plants exist the blossoming of which, accompanied by the production of pollen, produces allergic reactions for relatively long periods of the year. The article in question and the publications mentioned at the end of the latter are inserted by way of reference in the present disclosure.

An object of the present invention is to provide a protein possessing particular immunological properties. This protein is of use in combating allergic diseases and manifestations.

Thus the invention relates to a new product consisting of a protein having a molecular weight of about 14 000 and isoelectric point of about 4.6, its absorption spectrum having an absorption of $\epsilon=0.12$ units of optical density O.D., at 280 nm for an aqueous solution of 1 mg (dry weight) per ml of water.

Another object of the invention is to provide a process for isolating said protein from the pollen of a graminaceous plant, namely orchard grass.

Thus the invention has for further object to provide a process for obtaining a new protein product comprising putting the pollen, especially of graminaceous plant and preferably of orchard grass or *Dactylis glomerata* in contact with an aqueous medium, collecting the supernatent part, subjecting the soluble extract to a fractionating treatment and isolating the protein having a molar mass of about 14,000 g (molecular weight: 14,000 daltons) and an isoelectric point of about 4.6.

The starting plant material in the process of the invention is preferably a graminaceous plant termed *Dactylis glomerata*. The pollen of this plant is put in contact with an aqueous medium so as to provide a soluble fraction. The simplest manner of proceeding consists in placing the pollen in water and allowing it to incubate until the soluble fraction is extracted. It is advantageous to work at room temperature. The incubation period depends on the volume of the reaction medium employed. In practice, at room temperature, incubation periods of the order of one hour have been found suitable. The relative amounts of aqueous medium, in particular distilled water and orchard grass pollen, may vary within wide ranges. The weight of pollen in proportion to the volume of water may be from 10 to 200 parts by weight, for example of the order of 100 parts by weight per volume of water.

At the end of the incubation, the supernatent part is separated from the solid parts still present in the reaction medium and the soluble fraction is then fractionated so as to isolate the protein having the previously defined characteristics.

For the characterization of the new protein, there may be employed the isoelectrofocusing preparing technique described by RADOLA, B. J. (1973), Biochim. Biophys. Acta, 295, 412-428. This technique is known to one skilled in the art who may, if necessary, refer to this last bibliographical reference for the details of procedure. The fractionating method in question permits, by varying the pH, collecting the purified fractions in a thin layer of granulous gel (for example Sephadex or Biorad). When the soluble fraction extracted from the orchard grass pollen is treated with the considered technique, more than 60 bands are found to be present between pH 3.8 and 9. The protein according to the invention is separated at pH 4.6.

In an alternative embodiment, the new protein may be isolated by the chromatofocusing technique, such as that for example described in the printed article named "Chromatofocusing" distributed by Pharmacia Fine Chemicals AB Box 175 Uppsala Sweden; see also "Chromatofocusing isoelectric focusing on ion exchange columns", page 17-44 J. Chromatogr. 150 (1978).

The protein of the invention has particular immunological properties owing to its immunoregulating activity. Indeed, instead of inducing the synthesis of the homocytotropic IgE and IgG (for the definition of this expression see for example page 1010 of the work "Immunologie" by Paul Bordet (1972), Ed. Flammarion), specific immunoglobulins of the allergenic response, it strongly inhibits the synthesis of this class of immunoglobulins and only slightly diminishes that of the IgA, IgM and other IgGs. Investigations have shown in particular that the new protein is capable of inhibiting the synthesis of homocytotropic IgE and IgG after sensitization of a receiving organism with orchard grass pollen. These results show the specific activity of the immunoregulating protein according to the invention.

The protein according to the invention is therefore of utility in a therapeutic composition for allergic diseases and in particular pollinosis. Thus the invention concerns a therapeutic composition containing the protein defined hereinbefore as the active agent. More particularly, the invention concerns an immunoregulating therapeutic composition and an anti-allergic therapeutic composition containing said protein as the active agent.

Another object of the invention is to provide pharmaceutical compositions containing an effective quantity of the new protein in association with a pharmaceutically-acceptable vehicle suitable for the considered administration. For the administration, various routes, in particular, the oral, or parenteral route by inhalation or by injection are possible. It will be clear that the vehicles must be chosen differently in each of these routes. The galenical forms may be easily determined by one skilled in the art in accordance with the chosen mode of administration.

The new protein of the invention is very soluble in water. 5 mg of said protein are easily dissolved in 1 ml of water. It can be freeze-dried. The freeze-dried powder preserves all of the properties of the ordinary powder.

One skilled in the art will therefore understand that the product of the invention may be employed in very varied pharmaceutical compositions. Without the following indications having a limiting character, the composition may be in the form of injectable solutions. The product may also be in the form of a dry or freeze-dried powder, for example for the preparations suitable for inhalation, in particular in the form of an aerosol. The solid product may also be adsorbed on an adjuvant and be thus employed in an injection. Aqueous or oily compositions may also be envisaged for administrations by nasal/ophthalmic or oral instillation, or by inhalation. Other traditional galenical forms for oral administration may also be suitable, such as gelules, capsules, tablets, and like forms.

The therapeutic properties of the new protein act at small doses and no undesirable secondary effect has been found.

It will be observed that, for the envisaged applications, the protein of the invention has a group of very advantageous properties. It is the result of the fractionation of a product of natural origin, namely the pollen of a graminaceous plant. It is active at a low dose. Its toxicity is nonexistent in the normal conditions of application. Thus, when injected at the dose of 100 μg per mouse, namely 5 mg/kg by weight in man, no toxicity was found, whereas the most effective dose is at values which are 1/1000th of this value (0.1 μg instead of 100 μg in the mouse). This last property is very important, since the dangers of the use of unmodified allergens, for example of a total extract of pollen, are known. Very serious and even mortal accidents have occurred in the past when such products were injected in subjects suffering from allergy within the framework of a densitization treatment.

It is also of interest that the protein have a selective effect in the inhibition of antibodies formed by allergic reactions. The preferred field of utilization is that of the combatting of allergic reactions produced by the pollens of graminaceous plants.

In the adult man, a suitable posology for the treatment of pollinosis may range from 1 μg to 5 mg and is preferably of the order of 0.01 mg to be taken in a single injection.

By the oral route, doses of up to 10 mg are possible. For local application, the allowed doses may be as much as 100 mg.

The invention will now be illustrated, without in any way limiting the scope thereof, by the following description which gives an example of the isolation of the new protein from the pollen of orchard grass and the results of some pharmacological investigations.

EXAMPLE

Pollen from the graminaceous plant *Dactylis glomerata* is used. 50 mg of this pollen is incubated in 0.5 ml of distilled water for one hour at room temperature. The supernatent part is separated and the constituents of the soluble fraction of the pollen are fractionated by the preparative isoelectric focusing technique (see the aforementioned article of RADOLA). By this technique, between pH 3.8 and pH 9, the soluble fraction of the pollen is separated in more than 60 bands. A band whose molar mass is 14,000 g (molecular weight 14,000 daltons) and whose isoelectric point is 4.6, is recovered.

BRIEF DESCRIPTION OF THE FIGURE

The results of the fractionation are illustrated in FIG. 1 which is a diagram in which the values of the pH are plotted as abscissae and the fractionated products are plotted as ordinates. The protein according to the invention is isolated at pH 4.6.

The characteristic part of the adsorption spectrum of the new protein has an absorption $\epsilon$ of 0.12 units of O.D. at 280 nm for an aqueous solution of 1 mg (dry weight) per ml of water.

In a first series of tests, the anti-pollen response on laboratory animals was evaluated. These animals are female Balb/c mice. This breed was chosen because it has a good IgE response. In order to measure the quantity of antibody of type IgE, there was employed the passive cutaneous anaphylaxis test, abbreviated PCA, described by OVARY, Z., STEVEN, S., CAIZZA and SOMEI KOPINA (1975). Int. Archs. Allergy Appln. Imm., 48, 16–21. For the dosage of the antibodies of type IgM, IgG, IgA, there was employed the technique commonly known as the ELISA test, which is the abbreviation of the expression "Enzyme Linked Immunosorbent Assay" and is in particular described in the article by ENGVALL, E. and PERLMANN, P. (1971) Immunochemistry, 8,871. Hereinafter and for convenience, these measuring methods will be designated by their respective abbreviations PCA and ELISA.

Likewise, the total soluble fraction of the pollen of orchard grass is designated by the abbreviation SF. There was evaluated the immunity response of type IgE measured by PCA and of non-IgE type measured by ELISA, obtained by two injections by the intraperitoneal route and at intervals of 21 days of 10 μg of SF absorbed on 1 mg of $AlPO_4$. This immunization protocol was found to be optimum for the induction of IgE, anti-pollen of orchard grass. After injections of SF at 0 and 21 days, the protein (P) of the invention was injected on day 28. Table I at the end of the specifications shows the results obtained. Sub-table 1a concerns the inhibition of the anti-pollen response of type IgE, sub-table 1b relates to the inhibition of the anti-pollen response of the homocytotropic type IgG 1, and sub-table 1c illustrates the anti-pollen response of IgG, IgA, IgM and other IgG classes.

In sub-table 1a, the higher the titre revealed by the PCA, the higher the concentration of antibodies IgE, anti-SF of pollen of orchard grass. It can be seen that the protein (P) at doses of 1 μg/mouse and 0.1 μg/mouse inhibits the concentration of IgE anti-SF of orchard grass pollen.

In sub-tables 1b and 1c, the higher the titre of Ig measured by ELISA, the higher the concentration of antibodies of the considered class. It can be seen that the protein (P) at doses of 1 μg/mouse and 0.1 μg/mouse inhibits the amount of $IgG_1$, homocytotropic antibodies (sub-table 1b) but not in a significant manner the rate of antibodies of classes IgA, IgM, and the other IgG (see sub-table 1c).

Thus the results of table I show that the injection of the protein (P) in the presence of $AlPO_4$ in mice having received two injections of SF at 10 μg induces an inhibition both of the response IgE and the homocytotropic response IgG anti-SF. Further, there is no significant inhibition of the other classes of immunoglobulins. It is also found that the protein of the invention is effective at low doses.

It has also been found that the protein (P) induces no antibody response at doses ranging from 0.01 µg to 100 µg per mouse, even after two repeat injections. It is therefore found that the protein of the invention is devoid of an undesirable secondary effect under such conditions of use.

In a second series of tests, there was evaluated the absence of inhibition achieved by the protein of the invention of the allergic reaction produced by an injection of ovalbumin. The test animals were of the same type as those used in the first series. The ovalbumin was injected in the proportion of 1 µg per mouse on day 0. The protein (P) was injected on the 15th day. The results obtained are shown in the following table II.

TABLE 1

INHIBITION OF THE PRODUCTION OF IgE ANTI-POLLEN OF ORCHARD GRASS AND IgG, A AND M ANTI-POLLEN OF ORCHARD GRASS BY THE PROTEIN (P) OF THE INVENTION

1a - Inhibition of the anti-pollen response of type IgE by PCA in the mouse

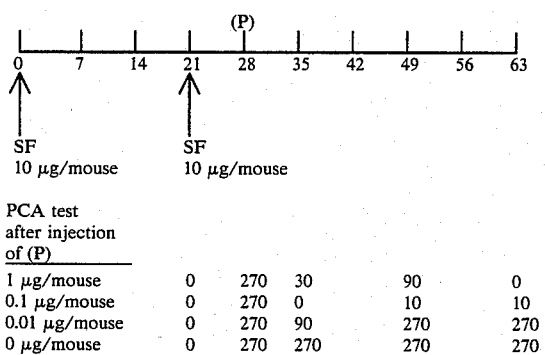

| PCA test after injection of (P) | | | | | | |
|---|---|---|---|---|---|---|
| 1 µg/mouse | 0 | 270 | 30 | | 90 | 0 |
| 0.1 µg/mouse | 0 | 270 | 0 | | 10 | 10 |
| 0.01 µg/mouse | 0 | 270 | 90 | | 270 | 270 |
| 0 µg/mouse | 0 | 270 | 270 | | 270 | 270 |

1b - Inhibition of the anti-pollen response of type IgG$_1$ by ELISA (results expressed in O.D. at 405 nm)

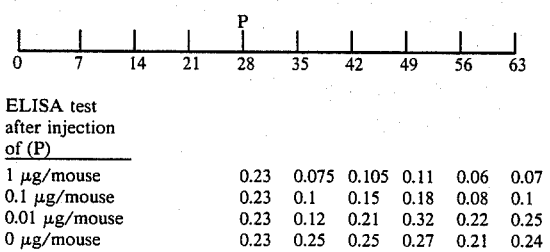

| ELISA test after injection of (P) | | | | | | |
|---|---|---|---|---|---|---|
| 1 µg/mouse | | 0.23 | 0.075 | 0.105 | 0.11 | 0.06 | 0.07 |
| 0.1 µg/mouse | | 0.23 | 0.1 | 0.15 | 0.18 | 0.08 | 0.1 |
| 0.01 µg/mouse | | 0.23 | 0.12 | 0.21 | 0.32 | 0.22 | 0.25 |
| 0 µg/mouse | | 0.23 | 0.25 | 0.25 | 0.27 | 0.21 | 0.24 |

1c - Anti-pollen response of the type IgA, IgM, and other IgG

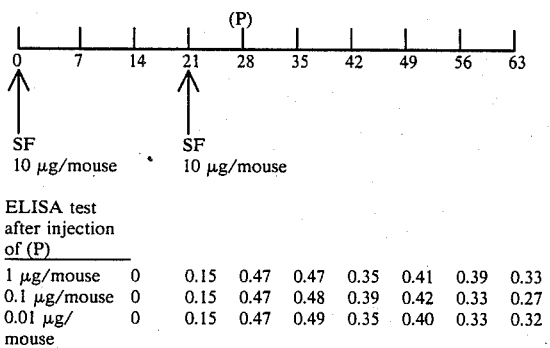

| ELISA test after injection of (P) | | | | | | | | |
|---|---|---|---|---|---|---|---|---|
| 1 µg/mouse | 0 | 0.15 | 0.47 | 0.47 | 0.35 | 0.41 | 0.39 | 0.33 |
| 0.1 µg/mouse | 0 | 0.15 | 0.47 | 0.48 | 0.39 | 0.42 | 0.33 | 0.27 |
| 0.01 µg/mouse | 0 | 0.15 | 0.47 | 0.49 | 0.35 | 0.40 | 0.33 | 0.32 |

TABLE 1-continued

INHIBITION OF THE PRODUCTION OF IgE ANTI-POLLEN OF ORCHARD GRASS AND IgG, A AND M ANTI-POLLEN OF ORCHARD GRASS BY THE PROTEIN (P) OF THE INVENTION

| 0 µg/mouse | 0 | 0.15 | 0.48 | 0.43 | 0.46 | 0.40 | 0.41 | 0.31 |

TABLE II

| | (P) | | |
|---|---|---|---|
| 0 | 9 | 15 | 21 days |
| I | I | I | I |
| OVA 1 µg/mouse in AlPO4 | | | |
| (P) 1 µg/mouse | 30 | 270 | 270 |
| (P) 0.1 µg/mouse | 30 | 270 | 270 |
| 0 (reference) | 30 | 270 | 270 |

In the present specification, the product of the invention was named "protein" for purposes of signification. However, the new product contains both amino acids and sugars and therefore constitutes a glycoprotein. Thirty one patients sensitive to gramineous pollen, 14 men and 17 women, were treated in May and June 1982 with only one 5 µg sub-cutaneous injection of the new protein in physiologic solution. Thirteen patients were treated between 3 and 1 weeks before the beginning of the pollinating season (in May) while 18 patients were treated between 1 to 3 weeks after the beginning of the pollinating season (in June). Twenty three patients have indicated to be better with regard to the previous pollinating seasons. The measuring of said improvement was followed by abstention of anti-allergic drugs for the patients treated in May and particularly by a decrease of such anti-allergic drugs by the patients treated at the beginning or during the pollinating season. Said decrease was regular during the 5 first days following the treatment and leading to discontinuation of anti-histaminic drugs or sodium cromoglycate one week after the treatment.

This clinical study shows that the product according to the invention is useful for treating pollinosis.

What we claim is:

1. A glycoprotein having a molecular weight of about 14,000 daltons and an isoelectric point of about 4.6; a 1 mg/ml aqueous solution of said glycoprotein having an absorption of $\epsilon = 0.12$ units of optical density at 280 nm; said glycoprotein being isolated by a process comprising:
   (a) admixing pollen of Dactylis glomerata with an aqueous medium, thereby extracting water-soluble products;
   (b) separating the aqueous extract from insoluble matter;
   (c) subjecting said aqueous extract to fractionation by molecular weight and isolectric point; and
   (d) isolating said glycoprotein.

2. A process for obtaining a glycoprotein comprising:
   (a) admixing pollen of Dactylis glomerata with an aqueous medium, thereby extracting water-soluble products;
   (b) separating the thus obtained aqueous extract from insoluble matter;
   (c) subjecting said aqueous extract to fractionation by molecular weight and isoelectric point; and (d) isolating the glycoprotein having a molecular weight of about 14,000 daltons and an isoelectric point of about 4.6.

3. A process according to claim 2, wherein the aqueous medium is distilled water.

4. A process according to claim 1, comprising operating at about room temperature.

5. A process according to claim 2, wherein step (c) is carried out by isoelectrofocusing.

6. A process according to claim 2, wherein step (c) is carried out by preparative chromatofocusing.

7. A process for obtaining a glycoprotein comprising
(a) admixing pollen of orchard grass or Dactylis glomerata with an aqueous medium, thereby extracting water-soluble products;
(b) separating the thus obtained aqueous extract from insoluble matter;
(c) subjecting the extract to fractionation by molecular weight and isoelectric point; and
(d) isolating the glycoprotein having a molecular weight of about 14,000 daltons and an isoelectric point of about 4.6.

8. A glycoprotein having a molecular weight of about 14,000 daltons and an isoelectric point of about 4.6; a 1 mg/ml aqueous solution of said glycoprotein having an absorption of $\epsilon = 0.12$ units of optical density at 280 nm; said glycoprotein being obtained by the process according to claim 7.

9. A method for inhibiting the synthesis of an immunoglobulin selected from the group consisting of homocytotropic IgE and IgG in a subject afflicted with increased production of said immunoglobulin, comprising administering to the subject an amount of a glycoprotein having a molecular weight of about 14,000 daltons, an isoelectric point of about 4.6, and an absorption of $\epsilon = 0.12$ units of optical density at 280 nm; effective to inhibit the synthesis of said immunoglobulins.

10. A pharmaceutical composition comprising:
(a) an effective quantity of a glycoprotein having a molecular weight of about 14,000 daltons, an isoelectric point of about 4.6, and an absorption of $\epsilon = 0.12$ units of optical density at 280 nm, for the treatment of pollinosis; and
(b) a pharmaceutically-acceptable vehicle adapted to oral or parenteral administration, or injection or inhalation.

11. The composition of claim 10, wherein the amount of the glycoprotein is between about 1 µg and 100 mg.

12. The composition of claim 10, in oral form, wherein the amount of the glycoprotein is up to about 10 mg.

13. The composition of claim 10 for topical application, wherein the glycoprotein is present in an amount of up to 100 mg.

14. The composition of claim 10, in injectable form, wherein the amount of the glycoprotein is between about 1 µg and 5 mg.

15. A pharmaceutical composition comprising:
(a) an amount of a glycoprotein having a molecular weight of about 14,000 daltons, an isoelectric point of about 4.6 and an absorption of $\epsilon = 0.12$ units of optical density at 280 nm effective for inhibiting the production of an orchard grass anti-pollen immunoglobulin selected from the group consisting of IgE and IgG; and
(b) a pharmaceutically-acceptable vehicle.

16. The composition of claim 10 in the form of an aerosol.

17. The composition of claim 10 in aqueous or oily form.

18. The composition of claim 17 in the form of a nasal, ophthalmic or inhalation preparation.

19. The composition of claim 12, in the form of gelules, capsules, or tablets.

20. A method of treating allergic reactions produced by the pollen of graminaceous plants, in a subject susceptible to said reactions, comprising administering to the subject an amount of a glycoprotein having a molecular weight of about 14,000 daltons, an isoelectric point of about 4.6, and an absorption of $\epsilon = 0.12$ units of optical density at 280 nm, effective for treating said allergic reactions.

* * * * *